United States Patent [19]

Umezawa et al.

[11] Patent Number: 4,716,221

[45] Date of Patent: Dec. 29, 1987

[54] 4'-DEMETHYL-4-EPIPODOPHYLLOTOXIN DERIVATIVE

[75] Inventors: Hamao Umezawa; Tomio Takeuchi, both of Tokyo; Shinichi Kondo, Yokohama; Wataru Tanaka, Hoya; Tomohisa Takita, Asaka; Yoshio Nishimura, Yokohama; Hiroshi Yoshikawa, Fujioka, all of Japan

[73] Assignee: Zaidan Hojin Biseibutsu Kagaku Kenkyu Kai, Tokyo, Japan

[21] Appl. No.: 842,286

[22] Filed: Mar. 21, 1986

[30] Foreign Application Priority Data

Apr. 2, 1985 [JP] Japan ................................ 60-68424

[51] Int. Cl.⁴ .............................................. C07H 15/24
[52] U.S. Cl. .................................. 536/17.2; 536/18.1
[58] Field of Search ............................... 536/17.2, 18.1

[56] References Cited

U.S. PATENT DOCUMENTS 3,524,844 8/1970 Keller-Juslen et al. ............. 536/18.1
4,275,192 6/1981 Apple et al. .......................... 536/6.4
4,547,567 10/1985 Umezawa et al. ................. 536/17.2

OTHER PUBLICATIONS

English translation of Japanese Patent Application No. 327881/1985, corresponding to U.S. Pat. No. 4,547,567.

Primary Examiner—J. R. Brown
Assistant Examiner—Elli Peselev
Attorney, Agent, or Firm—Banner, Birch, McKie and Beckett

[57] ABSTRACT

This invention relates to a novel 4'-demethyl-4-epipodophylltoxin derivative of the formula:

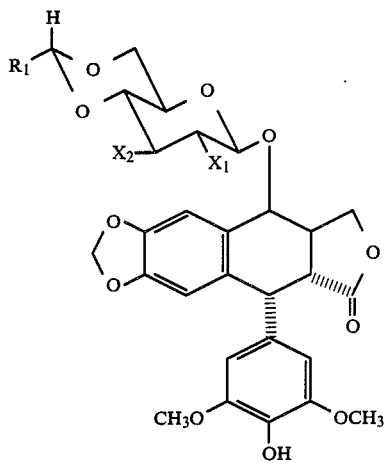

(wherein $R_1$ is a lower alkyl group; $X_1$ and $X_2$ are each a hydroxyl group or an amino group substituted by one or two lower alkyls, provided that either one of $X_1$ and $X_2$ is an amino group substituted by one or two lower alkyls and the other is a hydroxyl group) and salts thereof.

1 Claim, No Drawings

4'-DEMETHYL-4-EPIPODOPHYLLOTOXIN DERIVATIVE

BACKGROUND OF THE INVENTION

Heretofore, 4'-demethyl-epipodophyllotoxin-β-D-ethylidene glycoside (generally referred to as etoposide) has been known as a compound having antitumor activity (see, for example, U.S. Pat. No. 3,524,844).

The etoposide mentioned above exhibits an excellent anti-tumor activity but because of its extremely low solubility, considerable difficulty is currently involved in its administration to humans whether by injection or by oral route.

SUMMARY OF THE INVENTION

As a result of various studies made with a view to solving this problem, the present inventors have found that the novel 4'-demethyl-4-epipodophyllotoxin derivatives of formula (I) indicated below and salts thereof exhibit excellent anti-tumor activities, as well as high solubility in water. The present invention has been accomplished on the basis of this finding.

The term "lower alkyl" in the present invention means an alkyl group having 1 to 5, preferably, 1 to 3 carbon atom, which may be branched.

DETAILED DESCRIPTION OF THE INVENTION

The present invention relates to novel 4'-demethyl-epipodophyllotoxin derivatives of formula (I):

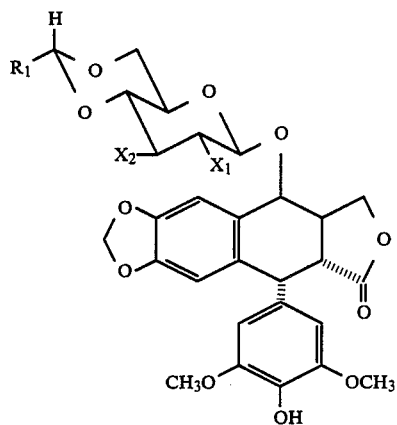

(wherein $R_1$ is a lower alkyl group; $X_1$ and $X_2$ are each a hydroxyl group or an amino group substituted by one or two lower alkyls, provided that either one of $X_1$ and $X_2$ is an amino group substituted by one or two lower alkyls, and the other is a hydroxyl group) and salts of such derivatives.

The 4'-demethyl-4-epipodophyllotoxin derivatives of formula (I) can be readily derived from unsubstituted amino sugar derivatives of formula (II):

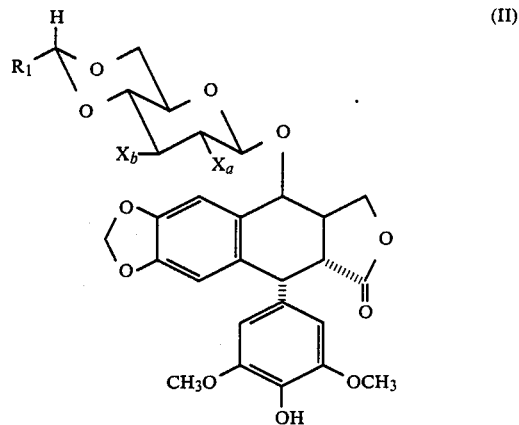

(wherein $R_1$ is a lower alkyl group; $X_a$ and $X_b$ are each of a hydroxyl group or an amino group, provided that either one of $X_a$ and $X_b$ is a hydroxyl group and the other is an amino group) (see Unexamined Published Japanese Patent Application No. 32799/1985). These unsubstituted amino sugar derivatives are reacted with aldehyde of formula (III): $R_2CHO$ (wherein $R_2$ is hydrogen or a lower alkyl group) in an inert solvent, and the resulting Schiff base is reduced with a metal-hydrogen complex compound, say, sodium borohydride, to provide the novel 4'-demethyl-4-epipodophyllotoxin derivatives of formula (I).

Examples of $R_1$ in formula (I) include methyl, ethyl, propyl and butyl groups, with methyl being particularly preferred. Examples of $R_2$ in formula (III) include hydrogen, methyl, ethyl and propyl groups.

Examples of the lower alkyl substituted amino group as $X_1$ or $X_2$ in formula (I) include di-loweralkyl-substituted amino groups such as dimethylamino and diethylamino groups, and mono-loweralkyl-substituted amino groups such as a mono-ethylamino group.

Examples of the metal-hydrogen complex compound suitable for use in the present invention include alkali metal borohydrides such as sodium borohydride, lithium borohydride, and potassium borohydride, cyanides and sulfides thereof such as sodium cyano borohydride and sodium borohydride-sulfur, as well as alkali metal aluminum hydrides such as lithium aluminum hydride.

The reaction between the unsubstituted amino sugar derivative of formula (II) and aldehyde of formula (III) may be carried out at a temperature between −40° C. and the boiling point of the solvent used, preferably about 0°–100° C. and is generally performed at room temperature.

The amount of aldehyde of formula (III) generally ranges from about 0.5 to 5 moles per mole of the unsubstituted amino sugar derivative of formula (II). If the aldehyde is used in an amount of from about 0.5 to 1.5 moles per mole of the derivative of formula (II) the compound having a mono-loweralkyl amino group as $X_a$ or $X_b$ is the predominant reaction product, and if more than about 1.5 moles of aldehyde is used, the compound having a di-loweralkyl amino as $X_a$ or $X_b$ is predominant.

The reduction of the resulting Schiff base may be performed at a temperature between −40° preferably −20° C. and the boiling point of the solvent used, and is generally carried out in the temperature range of 5°–30° C.

Any inert solvents may be used in the reaction and acetonitrile or dichloromethane is generally used.

Compounds of the general formula (I) forms salts, preferably pharmaceutically acceptable salts, with acids. The acids suitable for forming the salts may be either inorganic or organic, so long as the salt is nontoxic. No special restriction is posed upon these inorganic and organic acids, but preferable inorganic acids are hydrochloric acid, sulfuric acid, nitric acid, and phosphoric acid; preferable organic acids are acetic, propionic, succinic, fumaric, maleic, malic, tartaric, glutaric, citric, benzenesulfonic, toluenesulfonic, methanesulfonic, ethanesulfonic, propanesulfonic, aspartic, and glutamic acids.

Typical examples of the compounds in accordance with the present invention are listed below:

(i) 4-O-(2-deoxy-dimethylamino-4,6-O-ethylidene-β-D-glucopyranosyl)-4'-demethyl-4-epipodophyllotoxin (compound No. 1);

(ii) 4-O-(2-deoxy-2-ethylamino-4,6-O-ethylidene-β-D-glucopyranosyl)-4'-demethyl-4-epipodophyllotoxin (compound No. 2); and (iii) 4-O-(3-deoxy-3-dimethylamino-4,6-O-ethylidene-β-D-glucopyranosyl)-4'-demethyl-4-epipodophyllotoxin (compound No. 3).

ADVANTAGES OF THE INVENTION

As is clear from the following experimental data, the compounds of the present invention exhibit excellent anti-tumor activities and a significantly increased water solubility than etoposide.

(1) Anti-tumor test

Mice were inoculated intraperitoneally with $10^5$ mouse leukemia L1210 cells. After 24 hours, a hydrochloride of compound No. 1 of the present invention as dissolved in a 5% aqueous glucose solution was administered intraperitoneally to the mice for 5 consecutive days on a one-administration-per-day basis. Following a 30-day observation, the percent life prolongation for the mice was determined by the following formula:

$$\text{Percent life prolongation} = \frac{\text{Average number of days of survival of the treated group}}{\text{Average number of days of survival of the control group}} \times 100$$

The control group was injected with a 5% aqueous glucose solution only and survived for an average of 7.8 days.

The life prolongation of the mice to which compound No. 1 was administered in a dose of 2.5 mg/kg/day was 385% upward and all of them survived the test.

The mice to which etoposide was administered in a dose of 10 mg/kg/day exhibited a life prolongation of 321% upward, and three out of the five animals survived the test. The life prolongation of the mice to which etoposide was administered in a dose of 5 mg/kg/day was 208%.

(2) Water solubility

The water solubility of etoposide is 0.1 mg/ml. In comparison, the solubility value for a hydrochloride of 4-O-(2-deoxy-2-dimethylamino-4,6-O-ethylidene-β-D-glucopyranosyl)-4'-demethyl-4-epipodophyllotoxin (compound No. 1) is 15 mg/ml upward.

The methods of synthesis of the compounds of the present invention are hereunder described in greater detail with reference to the following examples.

EXAMPLE 1

Synthesis of 4-O-(2-deoxy-2-dimehylamino-4,6-O-ethylidene-β-D-glucopyranosyl)-4'-demethyl-4-epipodophyllotoxin (compound No. 1)

Five hundred milligrams of 4-O-(2-amino-2-deoxy-4,6-O-ethylidene-β-D-glucopyranosyl)-4'-demethyl-4-epipodophyllotoxin was suspended in 5 ml of acetonitrile. To the suspension, 0.2 ml of a 37% aqueous formalin was added, and three portions of sodium cyano borohydride (150 mg in all) were added to the mixture over a period of 5 minutes.

After a 30-minute reaction, 100 ml of dichloromethane was added to the reaction mixture, which was then washed with 30 ml of water. The organic layer was dried over anhydrous $Na_2SO_4$ and concentrated. The concentrate was isolated and purified by silica gel chromatography, producing 430 mg of 4-O-(2-deoxy-2-dimethylamino-4,6-O-ethylidene-β-D-glucopyranosyl)-4'-demethyl-4-epipodophyllotoxin.

mp., 196°–198° C. (crystallized from acetone) specific rotation: $[\alpha]_D^{23}$—114° ($CHCl_3$) MS SIMS 616 $(M+H)^+$ NMR ($CDCl_3$)

δ 1.41 (3Hd, $CH_3$)

δ 2.26 (6Hs, $N(CH_3)_2$)

δ 3.76 (6HS, $-OCH_3$)

δ 6.01 (2Hs, $-O-CH_2-O-$)

δ 6.23 (2Hs, H-2',6')

δ 6.58 (1Hs, H-8)

δ 6.75 (1Hs, H-5)

EXAMPLE 2

Synthesis of 4-O-2-deoxy-2-ethylamino-4,6-O-ethylidene-β-D-glucopyranosyl)-4'-demethyl-4-epipodophyllotoxin (compound No. 2)

Sixty milligrams of 4-O-(2-amino-2-deoxy-4,6-O-ethylidene-β-D-glucopyranosyl)-4'-demethyl-4-epipodophyllotoxin was dissolved in 1 ml of acetonitrile. To the solution, 6 μl of acetaldehyde was added, and after cooling the mixture to −20° C., 15 mg of sodium cyano borohydride was added and reaction was carried out for 15 minutes. The reaction mixture was allowed to warm to room temperature, mixed with 20 ml of dichloromethane, and washed with 10 ml of water. The organic layer was dried over anhydrous $Na_2SO_4$ and concentrated. The concentrate was isolated and purified using a silica gel TLC plates, thereby producing 40 mg of 4-O-(2-deoxy-2-ethylamino-4,6-O-ethylidene-β-D-glucopyranosyl)-4'-demethyl-4-epipodophyllotoxin.

mp., 208°–210° C. (as HCl salt) specific rotation: $[\alpha]_D^{24}$−90° ($CHCl_3$) MS SIMS 616 $(M+H)^+$ Compound No. 3, i.e., 4-O-(3-deoxy-3-dimethylamino-4,6-O-ethylidene-β-D-glucopyranosyl)-4'-demethyl-4-epipodophyllotoxin, can be obtained by repeating the procedures described above except that the 4-O-(2-deoxy-2-amino-4,6-O-ethylidene-β-D-glucopyranosyl)-4'-demethyl-4-epipodophyllotoxin is replaced by 4-O-(3-deoxy-3-amino-4,6-O-ethylidene-β-D-glucopyranosyl)-4'-demethyl-4-epipodophyllotoxin.

What is claimed is:

1. 4-O-(2-deoxy-2-dimethylamino-4,6-O-ethylidene-β-D-glucopyranosyl)-4'-demethyl-4-epipodophyllotoxin and salt thereof.

* * * * *